United States Patent [19]

Tuan et al.

[11] Patent Number: 5,126,260
[45] Date of Patent: Jun. 30, 1992

[54] HUMAN ERYTHROID-SPECIFIC TRANSCRIPTIONAL ENHANCER

[75] Inventors: Dorothy Y. H. Tuan, Newton; Irving M. London, Cambridge, both of Mass.; William B. Solomon, New York, N.Y.

[73] Assignee: Massachusetts Institute of Technology, Cambridge, Mass.

[21] Appl. No.: 622,356

[22] Filed: Dec. 4, 1990

Related U.S. Application Data

[63] Continuation of Ser. No. 113,677, Oct. 26, 1987, abandoned, which is a continuation-in-part of Ser. No. 98,025, Sep. 17, 1987, abandoned.

[51] Int. Cl.$^5$ .................... C12N 15/85; C12N 5/16; C12N 15/00; C12P 21/02
[52] U.S. Cl. .................... 435/240.2; 435/320.1; 435/172.3; 435/69.1; 435/69.6; 935/34; 935/36; 935/70
[58] Field of Search .................... 435/320.1, 240.2, 91, 435/172.3, 69.1, 69.6; 536/27; 935/34, 36, 33, 70

[56] References Cited

U.S. PATENT DOCUMENTS 4,663,281 5/1987 Gillies et al. .................... 435/69.1
4,722,897 2/1988 Soeda et al. .................... 435/69.1

OTHER PUBLICATIONS

Pouwels et al., Cloning Vectors, (1985), VIII-A-a-i-5.
Chada, K. et al., Nature, 314:377-380 (1985).
Townes, T. et al., EMBO J., 4:1715-1723 (1985).
Rutherford, T. and A. Nienhuis, Mol. and Cell Biol., 7:398-402, (Jan. 1987).
Costantini, F. et al., Science, 233:1192-1194 (1986).
Magram, J. et al., Nature, 315:338-340 (1985).
Edlund, T. et al., Science, 230:912-916 (1985).
Pinkert, C. et al., Genes and Development, 1:268-276 (1987).
Banerji, J. et al., Cell, 27:299-308 (1981).
Bosze, Z. et al., EMBO J., 5:1615-1623 (1986).
Tuan, D. et al., Proc. Natl. Acad. Sci. USA, 82:6384-6338 (1985).
Tuan, D. and I. M. London, Proc. Natl. Acad. Sci. USA, 81:2718-2722 (1984).
Li, Q. I. et al., J. Biol. Chem., 260:14901-14910 (1985).
Cone, R. and R. Mulligan, Proc. Natl. Acad. Sci., 81:6349-6353 (1984).
Banjeri, J. et al., Cell, 33:729-740 (1983).
Tuan, D. et al., in Developmental Control of Globin Gene Expression, A. R. Liss, Inc., pp. 211-220 (1987).
Kollias, G. et al., Cell, 46:89-94 (1986).
Dick, J. et al., Cell, 42:71-79 (1985).
Hawley, R. G. et al., Proc. Natl. Acad. Sci. USA, 84:2406-2410 (Apr. 1987).
Acuto, S. et al., Biochem. Biophys. Res. Comm., 143:1099-1106 (Mar. 1987).
Behringer, R. R. et al., PNAS, 84:7056-7060 (1987).
Trudel, M. and F. Constantini, Genes and Development, 1:954-961 (1987).
Grosveld, F. et al., Cell, 51:975-985 (Dec. 24, 1987).
Forrester, W. C. et al., Nuc. Acids Res., 15:10159-10177 (1987).

Primary Examiner—Richard A. Schwartz
Assistant Examiner—Richard M. Lebovitz
Attorney, Agent, or Firm—Lahive & Cockfield

[57] ABSTRACT

A human erythroid specific enhancer element is described. The enhancer element can be used to enhance transcription of a structural gene in erythroid cells. Methods for gene therapy employing the enhancer element are also disclosed.

26 Claims, 8 Drawing Sheets

```
AAGCTTCAGTTTTTCCTTAGTTCCTGTTACATTTCTGTGT
GTCTCCATTAGTGACCTCCCATAGTCCAAGCATGAGCAGT
TCTGGCCAGGCCCCTGTCGGGGTCAGTGCCCCACCCCCGC
CTTCTGGTTCTGTGTAACCTTCTAAGCAAACCTTCTGGCT
CAAGCACAGCAATGCTGAGTCATGATGAGTCATGCTGAGG
CTTAGGGTGTGTGCCCAGATGTTCTCAGCCTAGAGTGATG
ACTCCTATCTGGGTCCCCAGCAGGATGCTTACAGGGCAGA
TGGCAAAAAAAGGAGAAGCTGACCACCTGACTAAAACTC
CACCTCAAACGGCATCATAAAGAAAATGGATGCCTGAGAC
AGAATGTGACATATTCTAGAATATATTATTTCCTGAATAT
ATATATATATATATACACATATACGTATATATATAT
ATATATATATTTGTTGTTATCAATTGCCATAGAATGATTA
GTTATTGTGAATCAAATATTTATCTTGCAGGTGGCCTCTA
TACCTAGAAGCGGCAGAATCAGGCTTTATTAATACATGTG
TATAGATTTTTAGGATCTATACACATGTATTAATATGAAA
CAAGGATATGGAAGAGGAAGGCATGAAAACAGGAAAAGAA
AACAAACCTTGTTTGCCATTTTAAGGCACCCCTGGACAGC
TAGGTGGCAAAAGGCCTGTGCTGTTAGAGGACACATGCTC
ACATACGGGGTCAGATCT
```

```
AAGCTTCAGTTTTTCCTTAGTTCCTGTTACATTTCTGTGT
GTCTCCATTAGTGACCTCCCATAGTCCAAGCATGAGCAGT
TCTGGCCAGGCCCCTGTCGGGGTCAGTGCCCCACCCCCGC
CTTCTGGTTCTGTGTAACCTTCTAAGCAAACCTTCTGGCT
CAAGCACAGCAATGCTGAGTCATGATGAGTCATGCTGAGG
CTTAGGGTGTGTGCCCAGATGTTCTCAGCCTAGAGTGATG
ACTCCTATCTGGGTCCCCAGCAGGATGCTTACAGGGCAGA
TGGCAAAAAAAAGGAGAAGCTGACCACCTGACTAAAACTC
CACCTCAAACGGCATCATAAAGAAAATGGATGCCTGAGAC
AGAATGTGACATATTCTAGAATATATTATTTCCTGAATAT
ATATATATATATATATACACATATACGTATATATATATAT
ATATATATATTTGTTGTTATCAATTGCCATAGAATGATTA
GTTATTGTGAATCAAATATTTATCTTGCAGGTGGCCTCTA
TACCTAGAAGCGGCAGAATCAGGCTTTATTAATACATGTG
TATAGATTTTTAGGATCTATACACATGTATTAATATGAAA
CAAGGATATGGAAGAGGAAGGCATGAAAACAGGAAAAGAA
AACAAACCTTGTTTGCCATTTTAAGGCACCCCTGGACAGC
TAGGTGGCAAAAGGCCTGTGCTGTTAGAGGACACATGCTC
ACATACGGGGTCAGATCT
```

HUMAN ERYTHROID-SPECIFIC TRANSCRIPTIONAL ENHANCER

This application is a continuation of application Ser. No. 113,677, filed Oct. 26, 1987, now abandoned, which is a continuation-in-part of U.S. patent application Ser. No. 98,025, filed Sep. 17, 1987, now abandoned.

BACKGROUND

Gene therapy for the thalassemia syndromes and hemoglobinopathies requires that the introduced globin gene mimic the function of an in situ normal globin gene both in tissue specificity and efficiency of transcription. See e.g., Anderson, W. F. (1984) Science 226, 401–409. DNA mediated gene transfer experiments have shown that the human beta-globin gene with its immediate 5' and 3' flanking sequences can be expressed in a manner that is specific for the tissue and the stage of development. Chada, K. et al. (1985) Nature 314:377–380; Townes, T. et al. (1985) EMBO 4, 1715-1723; Kollias, G. et al. (1986) Cell 4b, 89–94; Rutherford, T. and Nienhuis, A. (1987) Mol. and Cell Biol. 7, 398-402; Constantini, F. et al. (1986) Science 233, 1192-1194; Magram, J. et al. (1985) Nature 315, 338-340. However, the transcriptional efficiency of such an introduced beta-globin gene is generally low (see references cited supra). A high level of transcription may require yet another level of cis control exerted by sequence elements, such as the enhancer sequences, that do not reside in the globin structural gene and its immediate flanking sequences (Kollias, G. et al., supra).

In the transgenic mouse, for example, low level but tissue-specific and even developmental-stage specific expression of the beta-globin gene has been flanking sequence was injected into the mouse zygotes. The expression level of the introduced beta-globin gene in erythroid cells of the transgenic mice is very low-less than a few percent of that of the endogenous mouse beta-globin gene. In a few transgenic mice, however, the m-RNA transcribed from the injected beta-globin gene has been reported to be as high as 50% of the endogenous mouse beta-globin mRNA (see Townes, T. et al. and Constantini, F. et al., supra.). In such cases, multiple copies (20-50 copies) of the injected beta-globin gene have been found to be integrated into the host chromosome. High level accumulation of the transcripts from these integrated genes may be the result of either the cumulative effect of many such integrated genes transcribed at low rates or of the chance integration of a copy of the introduced gene into an activated host chromosomal site. This position effect, i.e., the dependence of the expression level on the transcriptional activity of the site of integration, suggests that yet another level of cis transcriptional control located farther away from the gene and its immediate flanking sequences such as may possibly be exerted by an enhancer element, is required for efficient transcription of an introduced beta-globin gene.

Enhancer elements have been identified in the viral SV40 genome (Bernolst, C. and Chambon, P. (1981) Nature 290:309-310) and in the eukaryotic immunoglobulin gene cluster (See e.g., Gillies, S. et al. (1983) Cell 33, 717-728; Banerji et al. (1983) Cell 33, 729–740; Mercola, M. et al. (1983) Science 221, 663–665; Queen, C. and Baltimore D. (1983) Cell 33, 741-748; Picard, P. and Schaffner W. (1983) Nature 307 80-82; Gillies, S. and Tonegawa, S., U.S. Pat. No. 4,6763,281). They are capable of transcriptionally activating cis-linked genes over long distances, and their action is independent of the orientation of the enhancer element, and of its position with respect to the gene. In contrast to the SV40 viral enhancer which exhibits wide cell type specificity, the Ig enhancer and other identified eukaryotic enhancer elements display tissue specificity: the Ig enhancer appears to be most active in lymphoid cells (see references cited immediately above), the insulin enhancer element, in pancreatic beta cells (Edlum, T. et al. (1985) Science 230, 912), and an albumin enhancer, in liver cells (Pinkert, C. et al. (1987) Genes and Development 1, 268).

High level transcription of the transfected beta-globin gene can indeed be achieved by the presence in cis of the SV40 enhancer (see e.g., Banerji, J. et al. (1981) Cell 27, 299-308.) or the immunoglobulin (Ig) gene enhancer (Banerji, J. et al. (1983) Cell, 33:729-740). The tissue specific expression of such enhancer-beta globin gene constructs is, however, dictated by the host range of the cis enhancer, such that the beta-globin gene driven by the Ig enhancer is expressed most efficiently not in erythroid but in lymphoid cells (Banerji et al., (1983) Cell 33:729-740). This suggests not only that high level expression of the transfected beta-globin gene requires the presence of a cis enhancer but also that the tissue specific element contained in the enhancer can override the tissue specificity of the promoter.

The Friend Leukemia virus, which induces erythroleukemia, has been reported to contain erythroid specific enhancer elements in its long terminal repeats (LTR's) (Booze, Z. et al. (1986) EMBO 5, 1615–1623). Because of the carcinogenic property of the viral sequences, the applicability of this erythroid specific viral enhancer element to gene therapy appears limited. Although the existence of erythroid-specific enhancers has been postulated, no such enhancer has been identified in mammalian cells. Tuan et al. examined major DNase I-hypersensitive sites in the human "beta-globin-like" gene domain and showed that they were located in DNA regions which have certain characteristics of enhancers. (See Tuan, D. et al. (1985) Proc. Natl. Acad. Sci. USA 82, 6384-6388; Tuan D. and London, I. M. (1984) Proc. Natl. Acad. Sci. USA 81, 2718-2722).

Retroviral vectors offer unique advantages over conventional methods for introduction of genes into host cells, such as hematopoietic cells, since they can be used to introduce an intact single copy of a gene into most mammalian cell types at much higher efficiencies, sometimes approaching 100%. (Weiss, R. et al. (1985) RNA Tumor Viruses, 2nd Ed., Cold Spring Harbor Laboratories, Cold Spring Harbor, N.Y.). Construction of enhancerless retroviral vectors in which the viral enhancer sequences are deleted from both the LTRS of the provirus, yields proviruses that are transcriptionally inactive, thus freeing the genomic insert in such vectors from the potential effects of vector transcription (Cone, R. et al (1987) Mol. and Cell Biol. 7, 87). The absence of enhancer sequences in both LTRs of the integrated provirus should also minimize the possibility of activating cellular proto-oncogenes and may thus provide a safer alternative in human gene therapy.

An enhancerless retroviral vector, which comprises: (1) an intact 5' LTR (2) a 3' LTR with a deletion in the retroviral enhancer sequence (3) a human beta-globin gene insert and (4) a selectable marker gene, the bacterial neomycin phosphotransferase gene (Neo ®), has been constructed (Cone, R. et al., supra.). In the absence of a transcriptional enhancer element, the transduced human beta-globin gene, even though efficiently introduced by retroviral infection into the host cells, is inefficiently expressed, at a level about 500-fold less than the endogenous beta-globin gene (Cone et al., supra.) Another variant construct of the enhancerless retroviral vector contains the selectable Neo ® gene and a c-myc oncogene coupled to the kappa immunoglobulin gene enhancer-promoter combination which confers B cell specific expression on cis linked genes (Dick, J. et al. (1985) *Cell* 42, 71). The c-myc gene in this vector was found to be transcribed in a B cell line infected with this recombinant retrovirus (Hawley, R. et al. (1987) *Proc. Natl. Acad. Sci.* 84, 2406).

Hematopoietic cells, infected with recombinant retroviruses, when injected into unirradiated or irradiated host animals, were found to be capable of long-term reconstitution of the marrow cells of the recipient animals. Hawley et al., supra, Lemishka, I. et al. (1986) *Cell* 45, 917.

SUMMARY OF THE INVENTION

Figure 1:
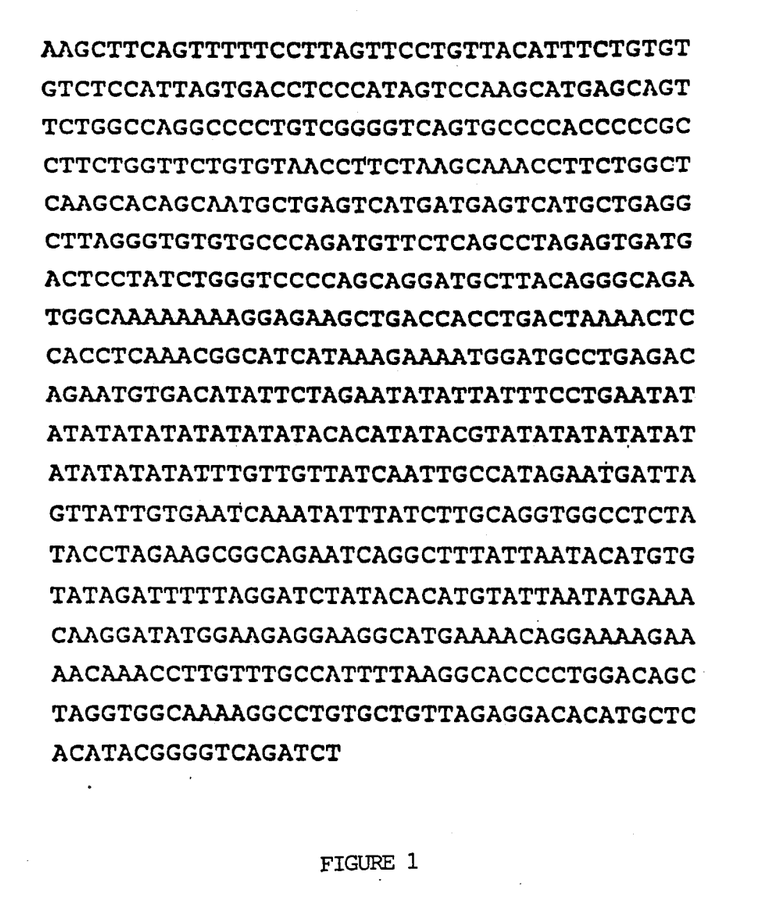
FIG. 1 shows the nucleotide sequence of the erythroid-specific enhancer element.

This invention pertains to a human transcriptional enhancer element which functions to increase transcription of genes in erythroid cells. The erythroid-specific enhancer element corresponds to an enhancer sequence (of about 800 nucleotide units in length) located in the human genome about 10.3–11.1 Kb upstream of the epsilon-globin gene and about 53.0–53.8 Kb upstream of the beta-globin gene. The nucleotide sequence of this natural enhancer is shown in FIG. 1. Preferred enhancer elements of this invention comprise DNA segments substantially homologous to at least a portion of this sequence.

The enhancer element can be combined with a transcription unit comprising one or more structural genes encoding a protein or proteins of interest (or precursors thereof) and appropriate regulatory sequences for these genes (e.g. promoter). The presence of the enhancer element leads to increased transcriptional efficiency of the structural gene (increased production of mRNA) in erythroid cell hosts. The increased transcriptional efficiency can provide for increased expression of the gene product in the recipient host cell. The enhancer element linked to a transcription unit can be incorporated into a vector such as a plasmid or virus which can be introduced into an erythroid cell by conventional techniques. The resulting transfected erythroid cells express the protein encoded by the transcription unit at high levels.

The enhancer element of this invention provides for improved genetic constructs for transfection of cells of the erythroid lineage. These constructs are designed for effective gene therapy of erythroid cell disorders such as the thalassemias and hemoglobinopathies.

BRIEF DESCRIPTION OF THE FIGURES

FIG. 2 (Part 2a and 2b) shows the construction of chloramphenicol acetyl transferase (CAT) plasmids with the CAT gene driven by the SV40 promoter.

FIG. 3 (Part 3a and 3b) shows the results of an assay of CAT activity in K562(3a) and HeLa cells (3b) of recombinant plasmids containing the CAT gene driven by the SV40 promoter.

FIG. 5 (Parts 5a and 5b) shows-construction of CAT plasmids (5b) with the CAT gene driven by the epsilon-globin promoter FIG. 6 (Parts 6a and 6b) shows CAT activities of recombinant CAT plasmids containing CAT gene driven by the epsilon-globin promoter in HeLa cells (6a) and K562 (6b).

DETAILED DESCRIPTION OF THE INVENTION

The enhancer element of this invention is a cis-control element which regulates the transcription of genes in human erythroid cells. The element is an 800 bp DNA segment located about 10.3–11.1 Kb 5' of the epsilon-globin gene and about 53.0–53.8 Kb 5' of the beta-globin gene.

The DNA sequence of the natural 800 bp enhancer element is shown in FIG. 1. (The region of the human genome 21 Kb upstream of epsilon-globin gene was sequenced by Qiliang Li et al. (1985) *J. Biol. Chem.* 260, 14901.) Preferred enhancer elements comprise DNA molecules substantially homologous to at least a portion of this sequence. Smaller portions of the 800 bp segment may also possess enhancer activity. Further, this enhancer sequence may be modified by base mutations including deletions, additions and substitutions. Accordingly the enhancer elements of this invention comprise any active DNA sequences having substantial homology to a region of the 800 bp sequence of the natural enhancer.

The enhancer element can be employed to provide improved genetic constructs for efficient expression of genes and the production of protein in erythroid cells. In erythroid host cells of transgenic mice, for example, the single transfected beta-globin gene, without a linked enhancer sequence, is calculated to be transcribed, on average, at one hundredth to one thousandth the transcriptional efficiency of the endogenous beta-globin gene: the transfected globin genes, present on average at a level of 20–50 copies per host cell, have been reported to produce an accumulated amount of beta-globin mRNA that ranges between 2% and 50% of that of the endogenous beta-globin gene. This calculated 100 to 1000 fold transcriptional enhancement appears to be required for the transfected beta-globin gene to be transcribed as efficiently as the endogenous beta-globin gene of the host erythroid cells. This degree of enhancement is within the range of enhancement that is achieved with the erythroid specific enhancer element of this invention.

In general, DNA constructs for transfection of cells comprise:

a. DNA comprising a transcription unit encoding a protein (or proteins) or a precursor thereof; and
b. a human erythroid-specific transcriptional enhancer element.

For assembly of the construct, the enhancer element for ligation to a transcription unit can be obtained from natural sources or by synthesis. For example, the enhancer element can be excised from human genomic DNA clones and then ligated with DNA comprising the transcription unit. Alternatively, the enhancer element can be synthesized according to the sequence provided in FIG. 1 by conventional techniques of DNA synthesis such as the phosphite triester chemistry (See e.g., Caruthers et al., U.S. Pat. No. 4,415,732; Sinha, N. D. et al., *Nucleic Acid Res.* X:4539 (1984).

In general, the enhancer element is placed in sufficient proximity to the transcription unit so that it is functionally active with the unit, i.e. so that it enhances the transcriptional efficiency of the structural gene. In some cases the enhancer can be placed distantly from the transcription unit. For example, in some constructs the enhancer can be placed at least 6 Kb from the transcription unit without loss of enhancer function. Optimal location of the enhancer can be determined by routine experimentation for any particular DNA construct. Function of the enhancer element is substantially independent of its orientation and thus the enhancer element can be placed in genomic or reverse genomic orientation with respect to the transcription unit. Generally, the enhancer element is placed upstream (5') of the transcription unit. However, in some constructs it may be positioned downstream (3') of the transcription unit.

The transcription unit comprises one or more structural genes encoding a protein (or proteins) of interest and a promoter (or promoters) and other regulatory sequences. Transcriptionally competent transcription units can be made by conventional techniques. The structural genes employed will generally encode erythroid proteins, but constructs can also be designed for expression of exogenous (nonerythroid) protein. Examples of erythroid proteins which have significance in gene therapy include human erythroid globin chains (e.g., beta-globins, gamma-globins, epsilon-globins, and alpha-like globins), erythroid enzymes or subunits thereof (e.g. glucose-6-phosphate dehydrogenase and pyruvate kinase) and erythroid cell structural proteins. Further, the genes may encode a precursor of the protein which is modified intracellularly after translation to yield the protein of interest.

Any suitable promoter may be used in the constructs. Although erythroid promoters are preferred for use in conjunction with structural genes encoding erythroid proteins, this may not always be optimal. The promoter normally associated with a structural gene which encodes the protein of interest is often desirable.

The DNA construct comprising the enhancer element ligated to a transcription unit encoding the protein of interest may be introduced into human erythroid cells by conventional procedures such as transfection, infection, microinjection, and electroporation. The DNA construct comprising the enhancer element ligated to the transcription unit may be inserted into or assembled within a vector such as a plasmid or virus. The construct can be assembled in or spliced into any suitable vector for incorporation into the host cell of interest. The vectors can contain a bacterial origin of replication so that they can be amplified in a bacterial host. The vectors can also contain an expressible gene encoding a selectable marker for selection of transfected cells. Preferred vectors for introduction of the construct are "enhancerless" (i.e. they lack native enhancer elements).

Vectors can be constructed which have the enhancer element placed in appropriate relation to an insertion site for receiving DNA encoding a protein. For example, such a vector can comprise:

a. an insertion region for insertion of DNA encoding a protein or precursor thereof; and
b. a human erythroid-specific transcriptional enhancer located in sufficient proximity to the insertion region to enhance transcription of an inserted DNA.

The insertion region can contain a restriction enzyme recognition site. The vectors can also contain a promoter upstream of the insertion site for insertion of a structural gene.

The erythroid specific enhancer element of this invention provides for improved gene therapy of human genetic diseases which are characterized by deficient expression of normal structural genes or expression of abnormal structural genes in erythroid cells. These diseases include: erythrocyte disorders related to abnormal globins (e.g., sickle cell disease and other hemoglobinopathies); anemias related to deficient synthesis of normal globin chains (e.g., the beta thalassemias); anemias due to increased destruction of erythrocytes with enzyme deficiencies (e.g., glucose-6-phosphate dehydrogenase deficiency and pyruvate kinase deficiency); and anemias due to increased destruction of erythrocytes with abnormal shape (e.g., hereditary elliptocytosis). The enhancer element provides a means for obtaining a high level of expression of a normal erythroid protein in erythroid cells and to bring about effective gene therapy of erythroid cell disorders. The constructs described above can be introduced into abnormal erythroid cells to compensate for production of an abnormal protein or protein which is either deficient or lacking in the cell.

In general, gene therapy of an erythroid cell disorder characterized by deficient or abnormal expression of an erythroid protein is carried out as follows. Bone marrow of the patient is removed (for example, by aspiration under sterile conditions). The bone marrow cells are then incubated with the vector with its DNA construct comprising a transcription unit encoding the normal erythroid protein (or precursor thereof) and the erythroid-specific transcriptional enhancer under conditions which allow the vector with its DNA construct to be incorporated into the cells. The treated bone marrow cells are then reinfused into the patient. The procedure can be repeated several times in order to increase the total number of marrow erythroid cells into which the normal gene has been introduced.

In gene therapy of human hemoglobin disorders of the beta chain of hemoglobin (where synthesis of a normal beta-globin chain is deficient or where an abnormal chain is synthesized) a vector-DNA construct containing a transcription unit encoding beta-globin and the transcriptional enhancer is incorporated into the bone marrow cells. Treatment of bone marrow cells will result in incorporation of the vector-DNA construct into erythroid precursor cells and hemopoietic stem cells.

Figure 7:
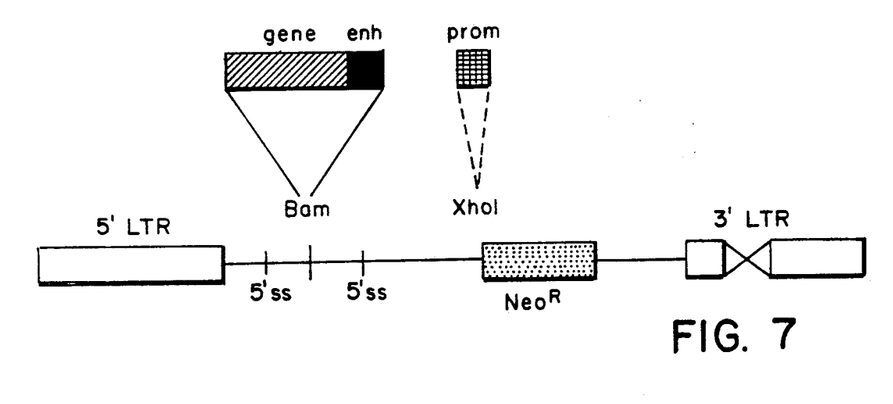
FIG. 7 shows the construction of the recombinant retroviral vector for introducing genes into hematopoietic cells.

A particularly useful vector for gene therapy is the retroviral vector. A recombinant retroviral vector can consist of the following parts (see FIG. 7):

i) An intact 5' LTR from MMLV, a murine leukemia retrovirus, followed by DNA containing the retroviral packaging signal sequence.
ii) The transcription unit to be introduced into erythroid cells for replacement gene therapy, coupled to the erythroid specific enhancer.
iii) A selectable gene, such as the Neomycin phosphotransferase gene (Neo ®) or the methotrexate-resistant dihydrofolate reductase (dhfr) gene without an immediate 5' promoter. A variant construct may contain the selectable gene with an immediate 5' promoter (such as the mouse or human metallothionein or the SV40 promoter) that is active in the packaging cell line as well as in hematopoietic cells.

iv) A 3' LTR which contains a deletion in the viral enhancer region, or deletions in both the viral enhancer and promoter regions.

The recombinant retroviral vector DNA can be transfected into the amphotropic packaging cell line ψ-AM (Cone R. and Mulligan, R. (1984) *Proc. Nat'l Acad. Sci.*, 81, 6349) or other packaging cell lines which are capable of producing high titer stocks of helper-free recombinant retrovirus. After transfection, the packaging cell line is selected for resistance to the drug G418, present at appropriate concentration in the growth medium. Only cells which have incorporated the recombinant retroviral DNA will be able to survive in the selection medium, since the neoR gene in the recombinant retroviral vector will be driven by the intact viral enhancer-promoter sequences present in the 5' LTR and by the immediate 5' non-viral promoter when it is present. Individual G418 resistant clones can be picked and expanded to select for clones which produce high viral titers.

Bone marrow cells can be infected by either co-cultivation with the G418 resistant viral producing cell line or by purified retroviruses according to conventional methods. The provirus, produced by reverse transcription from the viral genome and integrated into the chromosome of the infected hematopoietic cells, will not contain the viral enhancer sequence in either the 5' or the 3' LTR. The spliced structural gene, i.e. the transcriptional unit, will thus be free of transcriptional regulation by the viral enhancer sequence, and will be expressed under transcriptional regulation by the cis-linked erythroid specific enhancer. When the hematopoietic cells are infected by retroviral constructs containing the selectable marker gene and an immediate 5' non-viral promoter, these cells can be grown in selective medium, such that 100% of the cells re-introduced into the patient will contain the recombinant proviral genome. The introduced gene will be actively transcribed only in infected erythroid cells as the gene is regulated by the cis-linked erythroid specific enhancer. Nonerythroid hematopoietic cells will also incorporate the recombinant provirus, but as a result of the erythroid specificity of the cis-linked enhancer, the gene will not be significantly expressed in nonerythroid cells.

DNA constructs containing enhancer sequences of this invention can also be introduced into primary cells at various stages of development including the embryonic and fetal stages. This can be done to effect gene therapy at early stages of development. It can also be done to produce transgenic animals. In addition, the constructs of this invention can be used to transform cell lines (e.g. erythroid cell lines) for production of proteins of interest in vitro.

The invention is illustrated by the following exemplification.

Exemplification

We have shown that a 1.9 Kb DNA fragment, containing the major DNase 1 hypersensitive site HS II at −10 Kb 5' of the epsilon-globin gene, possesses enhancer activity. The enhancer activity has been mapped to the 0.8 Kb of DNA directly underlying HS II in the 5' end of the 1.9 Kb fragment. This enhancer element, when in combination with the homologous epsilon-globin promoter, enhances CAT gene activity by about 300 fold. It appears to be erythroid specific and can be placed as far as 6 Kb away from the epsilon-globin promoter and still appears to retain enhancer function.

Enhancer activity is found in a 1.9 Kb DNA fragment spanning a major DNase 1 hypersensitive site −10 Kb 5' of the epsilon-globin gene when coupled to an SV40 promoter.

Guided by the location of four apparently erythroid specific DNase 1 hypersensitive sites (HS I-IV), at −6 to −20 Kb 5' of the epsilon-globin gene (Tuan, D. et al. (1985) *PNAS USA* 6384-88), we have identified a segment of DNA underlying HSII, at −10.3 to −11.1 Kb 5' of the epsilon-globin gene, to possess enhancer function.

Figure 2A:
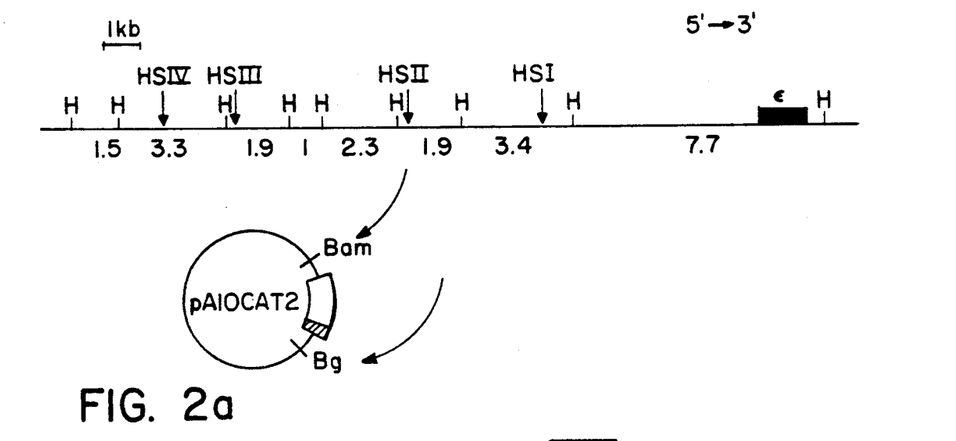

FIG. 2a shows the location, relative to the epsilon-globin gene, of the Hind III (H) fragment which spans the erythroid specific enhancer element underlying an erythroid specific hypersensitive site II (HSII) and of other Hind III fragments which span erythroid specific hypersensitive sites HSI, HSII, and HSIV or do not span any erythroid specific hypersensitive sites. After addition of Bam H1 linkers, these fragments were spliced into either the Bgl II (Bg) or the Bam H1 (Bam) site of pA10CAT2 plasmid.

Figure 2B:
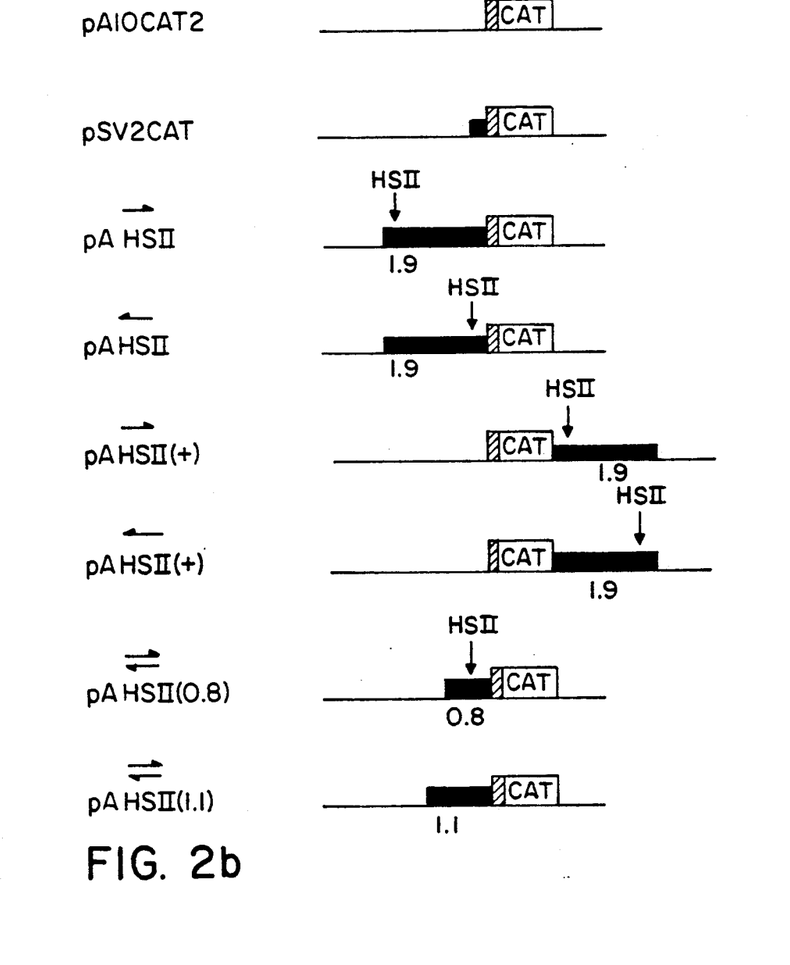
Figure 5A:
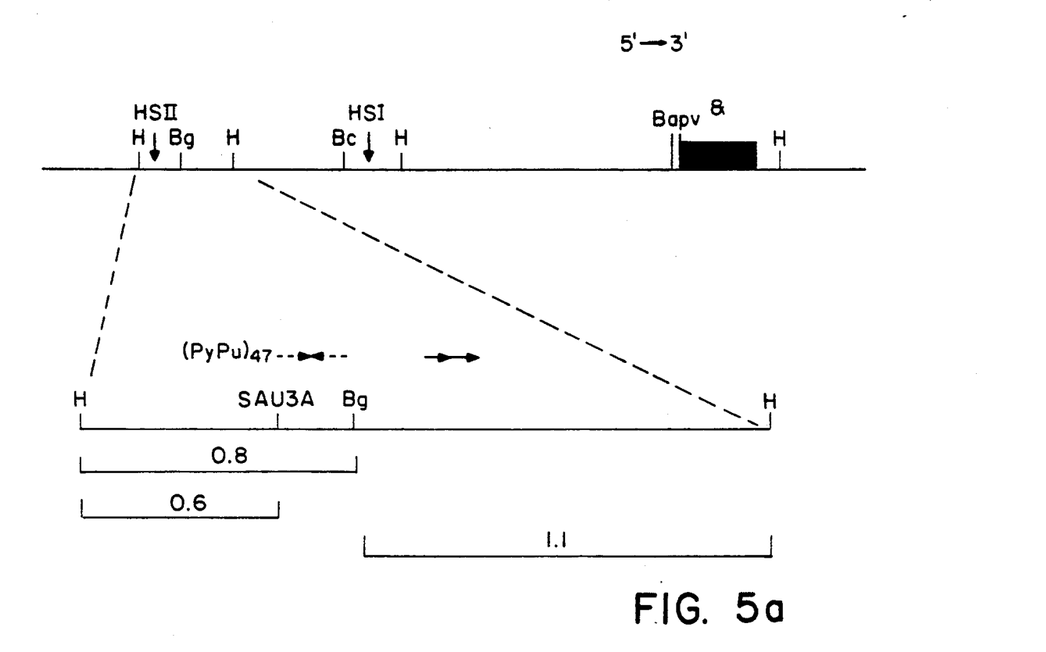
Figure 5B:
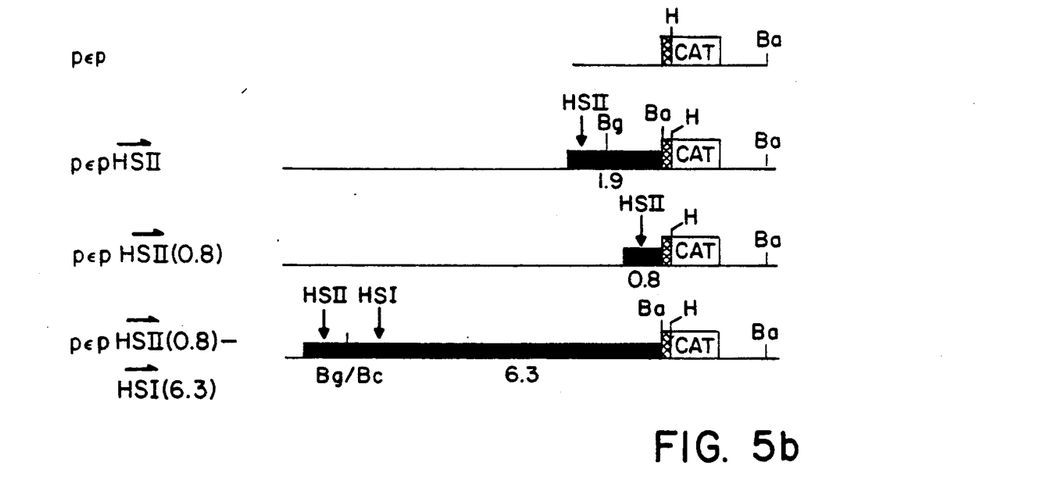

FIG. 2b shows partial linear maps of the control plasmids pA10CAT2 and pSV2CAT, and the various CAT plasmids containing the 1.9 KbDNA fragment spanning the enhancer element, or subfragments derived from this 1.9 Kb fragment. The hatched box represents the SV40 early promoter. The filled box in the pSV2CAT plasmid represents the SV40 enhancer sequence; in the other constructs, it represents various human genomic fragments tested for enhancer activity. The vertical arrow marks the location of the major DNase 1 hypersensitive site HSII, at −10 Kb 5' of the epsilon-globin gene. Horizontal half arrows denote the genomic (→) or reverse genomic orientation (←) of the spliced fragment. pAHSII (0.8) and pAHSII (1.1) were obtained by first digesting the Bam H1 linkered 1.9 Kb fragment with Bgl II (see FIG. 5) and then splicing the subfragment into the Bgl II site 5' of the CAT gene.

The enhancer contained in a 1.9 Kb fragment spanning HSII enhances, more than 50 fold, the transcription of a bacterial CAT gene, driven by an SV40 early promoter. In a similar construct, the DNA fragment containing HS I, at −6 KB 5' of the epsilon-globin gene, enhances CAT activity weakly, by about 2 fold. DNA fragments which span HS III and HS IV respectively, as well as the neighboring DNA fragments which do not span any hypersensitive sites, do not noticeably enhance CAT activity. In CAT plasmids driven by SV40 promoter, the enhancer effect of HS II shows both orientation and position dependence (FIG. 2 and Table 1) and appears most pronounced when spliced 5' of the CAT gene in reverse genomic orientation.

In addition, in such orientation, it does not show strict erythroid specificity, as it also activates the CAT gene in HeLA cells (Table 1), but it does not do so in the monocytic leukemia cell line THP-1 or in the promyelocytic leukemia cell line HL60. The lack of enhancer activity of this fragment in HL60 or THP-1 cells is not due to the failure of these cells to take up the transfecting plasmid DNA, nor is the observed enhancer activity in K562 and HeLa cells due to the fortuitous presence of more copies of the recombinant plasmid containing this fragment than the copies of the reference plasmid in the host cells (DNA dot-blot data not shown).

The enhancer activity is located in a 0.8 Kb fragment directly underlying HS II

In the attempt to improve the erythroid specificity as well as the transcriptional enhancing activity of the enhancer element, we divided the 1.9 Kb fragment into two subfragments: a 0.8 Kb subfragment derived from the 5' half, directly underlying HS II, and a 1.1 Kb subfragment from the 3' half, which does not span any erythroid specific DNase 1 hypersensitive site (FIG. 2). The respective fragment was spliced into the enhancerless pA10CAT2 (Gorman, C. et al. (1982) Mol. and Cell Biol. 2, 1044-1051) in both orientations and subsequently transfected into the erythroid K562 and non-erythroid HeLa cells.

Figure 3A:
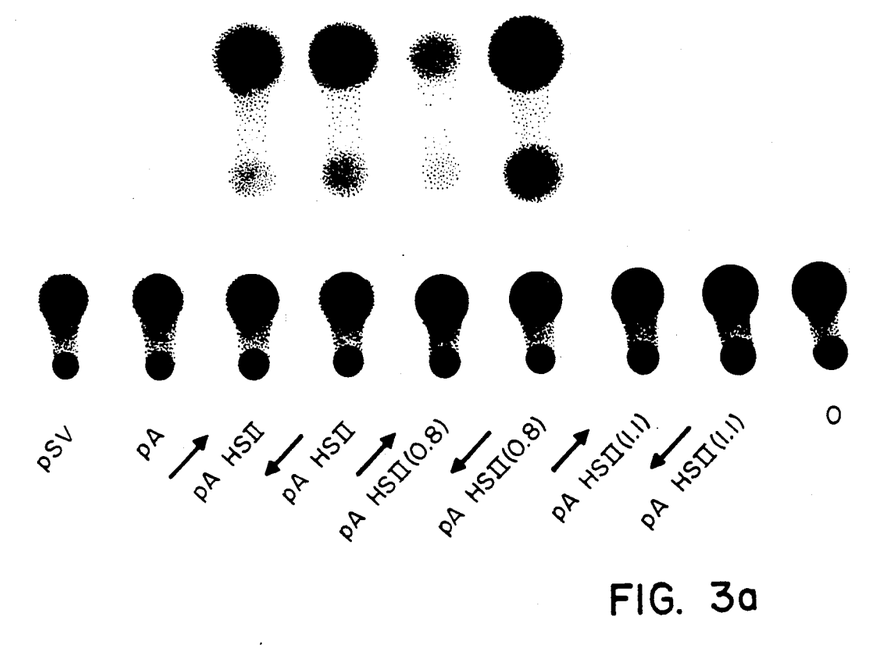
Figure 3B:
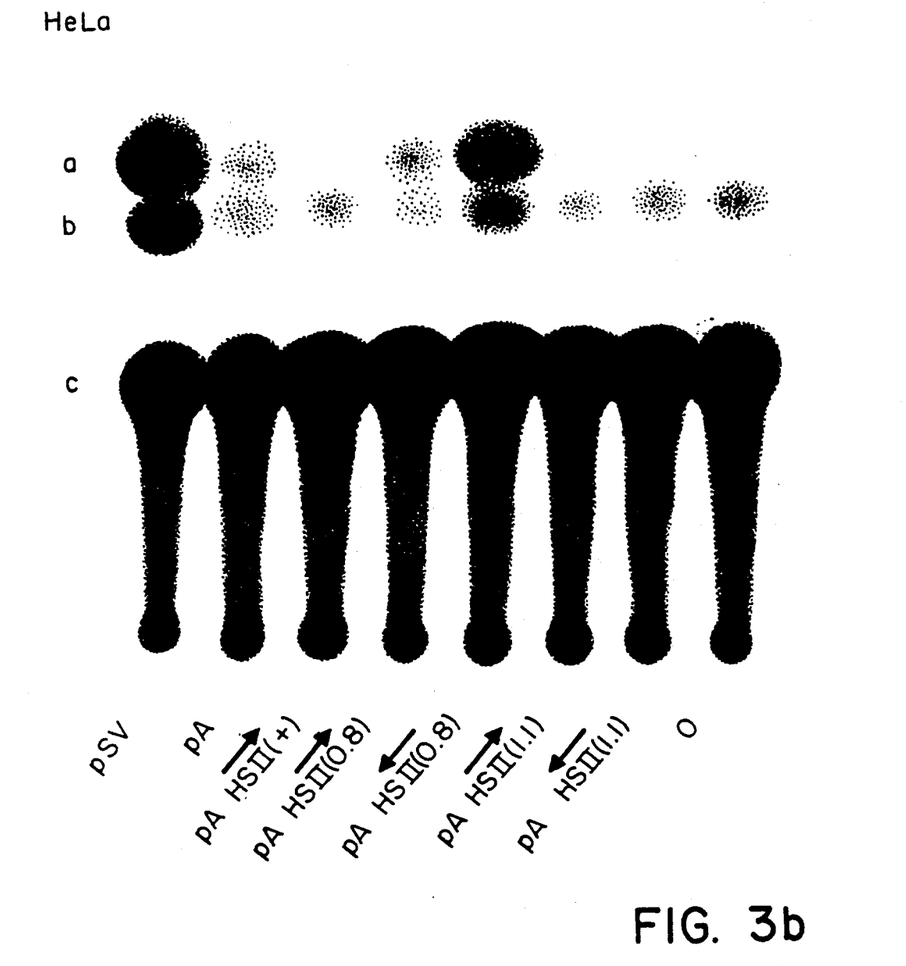

FIG. 3 shows the results of an assay of CAT activity in K562 and HeLa cells of recombinant plasmids containing the CAT gene driven by the SV40 promoter. K562 cells were maintained in medium containing 20 uM Hemin both before and after the transfection. The CAT assay was carried out as follows: Cell extracts from equal numbers of transfected cells were first heated at 65° C. for 10' to inactivate molecules which apparently interfere with the CAT enzymatic activity in the K562 cell extracts and were then incubated with $^{14}$C-chloramphenicol and acetyl CoA for 3 hrs at 37° C., with the addition of extra acetyl CoA every 45 minutes. The acetylated products (a,b) were separated from unreacted chloramphenicol (c) by thin-layer chromatography (TLC). The plates were exposed to X-ray film for 24-48 hrs. Each lane represents the CAT activity of the respective recombinant plasmid as marked. O=mock transfection.

From FIG. 3, it can be seen that the 0.8 Kb subfragment, which spans HS II, contains the enhancer activity, as tested in both K562 cells (FIG. 3a) and HeLa cells (FIG. 3b). The 1.1 Kb subfragment does not contain noticeable enhancer function. In K562 cells the 0.8 Kb subfragment, in reverse genomic orientation, exhibits, as does the parental 1.9 Kb fragment, 3-5 fold more enhancer activity than the same subfragment in genomic orientation (Table 1). Again it does not show strict erythroid specificity, as it also enhances CAT gene expression in HeLa cells (FIG. 3b).

The pronounced orientation dependence, i.e. the much higher transcriptional enhancing activity of the 0.8 Kb fragment in the reverse genomic orientation, posed the possibility that a promoter sequence, which functions in an orientation dependent manner, rather than an enhancer sequence, might reside in this fragment. Preliminary S1 nuclease mapping of RNA's isolated from HeLa cells transfected with PA HSII (0.8) which contains in a 5' to 3' direction HSII (0.8)—SV40 early promoter—CAT gene (FIG. 2) is shown in FIG. 4.

Figure 4:
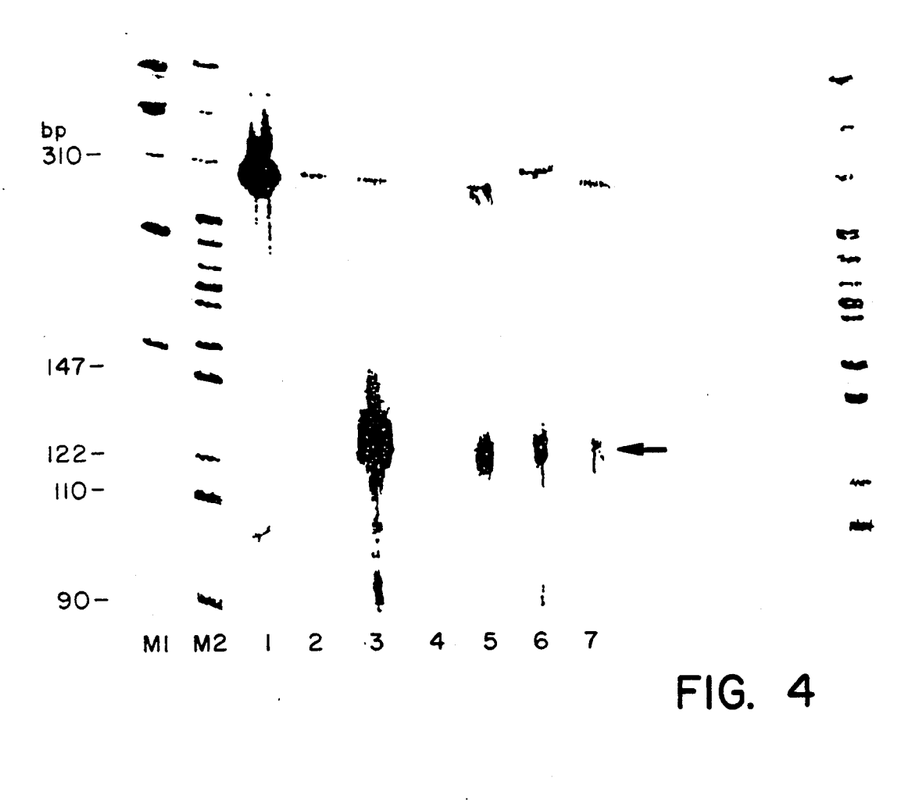
FIG. 4 shows S1 nuclease mapping of the initiation site of CAT transcripts in RNA isolated from transfected HeLa cells.

FIG. 4 shows S1 nuclease mapping of the initiation site of CAT transcripts in RNA isolated from transfected HeLa cells. RNA was isolated by the guanidine isothiocyanate method (Chirgwin, J. M. et al. (1979) Biochem 18, 5294.). S1 nuclease mapping was carried out as described (Berk, A. and Sharp, P. (1977) Cell 12, 721; Weaver, R. and Weissmann, C. (1979) Nucl. Acids Res. 6, 1175-1192). The probe was made as follows: a 20-mer oligonucleotide primer from within the nontranscribing strand of the CAT gene (a gift from Dr. A. Baldwin) was labeled at the 5' end by polynucleotide kinase. The kinased oligonucleotide primer was hybridized to denatured pA10CAT2, the template, and extended in the presence of Klenow fragment and the 4 unlabeled deoxynucleotides, then cut with BglII, followed by alkaline gel electrophoresis to produce a single stranded probe of approximately 300 bp labeled at the 5' end, which will hybridize to CAT transcripts. Lanes M1 and M2: molecular size markers. Lanes 1 and 2: the probe before and after S1 nuclease digestion. The length of probe-protected CAT transcripts as produced by pSV2CAT (lane 3) by pA10CAT2 (lane 4), by pAHSII (0.8) (lane 5), by pAHSII (0.8) (lane 6) and by pAHSII (+) (lane 7). The horizontal arrow marks the predominant length of the protected CAT transcripts.

The results show that the CAT transcript in the RNA's isolated from cells transfected with pSV2CAT and pAHSII (0.8) all produced a protected fragment of about 130bp in length (lanes 3,5 and 6 in FIG. 4). Thus, the protected fragments produced by CAT transcripts of pAHSII (0.8) are of the same length as that by CAT transcripts of pSV2CAT, which contains 5'—the SV40 enhancer—SV40 promoter— CAT gene 3' (lane 3 in FIG. 4). Longer CAT transcripts initiated upstream of the SV40 early promoter from within the 0.8 Kb fragment in either genomic or reverse genomic orientation in pAHSII (0.8) were not detected (lanes 5 and 6 in FIG. 4). This suggests that no apparent promoter sequences reside in the 0.8 Kb fragment.

The much higher enhancer activity of the 0.8 Kb fragment in reverse genomic orientation may thus be due to the possibility that the actual enhancer element may be located in a much smaller DNA region toward the 5' end of this 0.8 Kb fragment and the 3' part of this fragment when interposed between the enhancer and the promoter, as in the genomic orientation, may be inhibitory to enhancer activity.

Recombinant CAT plasmids with the CAT gene driven by the embryonic epsilon-globin promoter.

The above plasmids which do not show strict erythroid specificity were all constructed in CAT plasmids containing the SV40 promoter with broad tissue specificity. We have constructed another set of recombinant CAT plasmids, using the embryonic epsilon-globin promoter to drive the CAT gene, to determine if the enhancer sequence contained in either the 1.9 Kb or the truncated 0.8 Kb fragment, would show stricter erythroid specificity, since globin promoters have been shown to confer erythroid specific expression on linked genes.

FIG. 5 shows construction of CAT plasmids with the CAT gene driven by the epsilon-globin promoter. Top horizontal line shows the restriction sites 5' of the epsilon-globin gene used in construction of the recombinant plasmids. H:Hind III, Bg:Bgl II, Bc:Bcl I, Ba:Bam H1, pV:pVUII. The next horizontal line shows the expanded 1.9 Kb Hind III fragment. Numbers below the horizontal lines represent sizes in Kb of the respective DNA fragments. The checkered box represents the epsilon-globin promoter. The enhancerless p p, with the epsilon-globin promoter 5' of the CAT gene was constructed by ligating a 200 bp BamH1-pvuII fragment containing the epsilon-globin promoter (Li, Q. L. et al. (1985) J. Biol. Chem. 260, 14901-14910), to the pA10-CAT2 plasmid from which the SV40 early promoter had been deleted by BglII-Stu1 double digestions. pεp HSII, or pεpHSII (not shown), was constructed by triple ligations of the BamH1 linkered 1.9 Kb fragment containing the enhancer element, the 200 bp BamH1-pvuII fragment containing the epsilon-globin promoter and the large BglII-StuI fragment containing the CAT gene from pA10CAT2. pεpH̃SII (0.8) was obtained by digesting the 1.9 Kb insert in pεpH̃SII with bglII and BamH1, which delete a 3' 1.1 Kb subfragment in the 1.9 Kb insert not containing any DNase 1 hypersensitive sites, and recircularization of the remaining large fragment. pεpdH̃SII (0.8)-H̃SI (6.3) was constructed by ligating the above linear, not recircularized BglII-BamH1 large fragment to a 6.3 Kb Bc1I-BamH1 fragment 5' of the epsilon-globin gene.

Figure 6A:
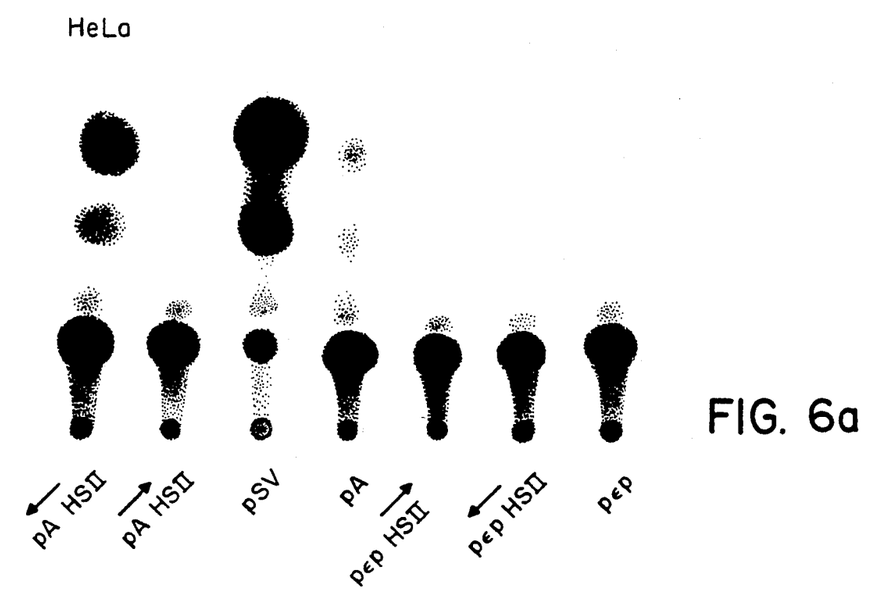
Figure 6B:
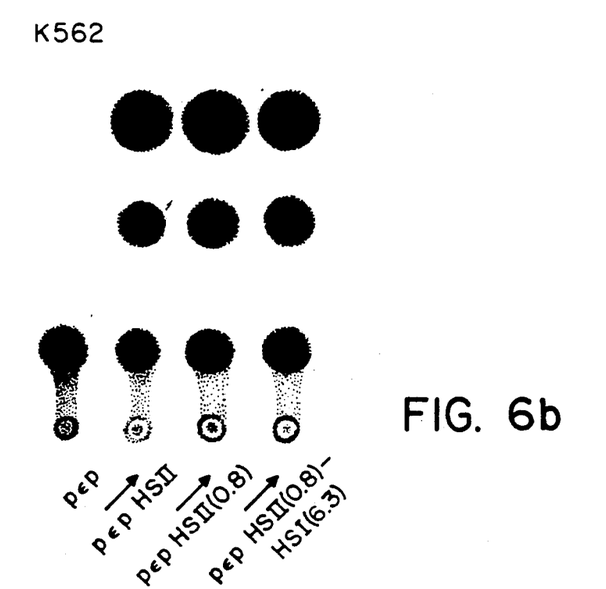

FIG. 6 shows CAT activities of recombinant CAT plasmids containing CAT gene driven by the epsilon-globin promoter. The same amount (20 μg) of each recombinant plasmid was used for transfection. The pεpH̃SII (0.8)-H̃SI (6.3) plasmid, with the large insert of 7 Kb, however, has about twice the molecular weight of the other plasmids, so the number of transfecting molecules in 20 μg, for this plasmid, is only about half as many as in 20 μg of other plasmids. The intensity of the acetylated spots in pεpH̃SII (0.8)-H̃SI (6.3), after correction for the number of transfecting molecules, should therefore be increased by approximately two fold. Pilot experiments have shown that the intensity of the acetylated spots increases in a linear fashion with respect to the amount of transfecting plasmid at least up to 20 μg per 10 cm dish of K562 cells.

In these constructs the 1.9 Kb fragment in either orientation does not appear to activate CAT gene in Hela cells (FIG. 6). Yet in K562 cells, both the 1.9 Kb (in pεp H̃SII and the 0.8 Kb fragments (in pεpH̃SII 0.8), even in genomic orientation, enhance CAT gene activity to similar levels of about 300 fold (FIG. 6, Table 1). This suggests that in combination with the homologous epsilon-globin promoter, the enhancer element 1) is more active than with the heterologous SV40 promoter; 2) appears to show stricter erythroid specificity since it does not activate CAT gene in HeLa cells; and 3) can be placed at least 1.1 Kb away from the epsilon-globin promoter and still retain the same degree of enhancer activity, since the enhancer activities of the 1.9 Kb and 0.8 Kb fragments, in pεpH̃SII and pεpH̃SII (0.8) respectively, are similar (Table 1).

To determine whether the enhancer element can be placed even farther away from the epsilon-globin promoter, and also whether DNA directly underlying HSI, which by itself does not show much enhancer function, but if linked in tandem with the enhancer element in HSII, can boost the enhancer function of HSII, we have constructed another plasmid (pεpH̃SII (0.8)-H̃SI (6.3)). In this plasmid, the enhancer element contained in the 0.8 Kb fragment is abutted by the DNA directly underlying HSI, followed by another 5.5 Kb of DNA naturally occurring between HSI and the epsilon-globin promoter in the genome (FIG. 5). The CAT activity by this plasmid, which enhances CAT gene activity by about 500 fold, is 40% more active than pεpH̃SII (0.8), containing only the 0.8 Kb fragment 5' of the ε-globin promoter and the CAT gene. This suggests that 1) the enhancer element in HSII can be placed as far as 6 Kb away from the epsilon-globin promoter and still retained enhancer activity; and 2) sequence elements in HSI or in the 5.5 Kb of more downstream DNA can boost the enhancer function of HSII.

The enhancer sequence is not species specific.

The human erythroid specific enhancer sequence, when coupled to an appropriate promoter sequence, is functional not only in human but also in mouse (MEL) erythroid cells (Table 1). This observation suggests that the human erythroid specific enhancer sequence is not species specific.

The construction of a recombinant vector for introducing genes into hemopoietic cells FIG. 7 shows a construction of a recombinant vector for introducing genes into hemopoietic cells. The figure is not drawn to scale. The stippled box represents a selectable marker gene (Neo ® is shown but others can be used). Horizontal arrows mark the direction of gene transcription. The checkered box represents the promoter sequence (metallothionein, SV40 or any other suitable promoter) which can be optionally spliced 5' of the selectable marker gene. The hatched box represents the gene to be spliced for replacement gene therapy, which as drawn is spliced into a unique Bam H1 (Bam) site, between the 5' and 3' viral splice sites (5'ss and 3'ss), in a transcriptional orientation opposite to that of the selectable marker gene and of the viral transcription. The filled box represents the erythroid specific enhancer element, to be spliced 5' of the gene for replacement gene therapy. The erythroid specific enhancer can also be spliced 3' of the gene. The enhancer-gene cassette, in appropriate orientation, can also be spliced into other restriction sites in the retroviral vector, provided such sites of insertion allow the transcription of the gene in the cassette to be regulated by the erythroid specific enhancer and to be free of undesirable regulatory influences by other vector sequences.

TABLE 1

| Plasmids | K562 | HeLa | THP-1 | HL60 | MEL |
|---|---|---|---|---|---|
| pA10CAT2 | | 1 | 1 | 1 | 1 |
| pSV2CAT | 0.9 | 160 ± 40 | 2.3 ± 1.1 | 0.8 | 28 ± 3 |
| pA ⃖ HSII | 66.5 ± 22 | 8.8 ± 5 | 0.4 ± 0.25 | 1.1 | 3 ± 1 |
| pA ⃗ HSII | 26 | 0.7 ± 0.3 | | 1.0 | 18 ± 11 |
| pA ⃖ HSII-(0.8) | 88 ± 45 | 13 | | | 18 |
| pA ⃗ HSII-(0.8) | 14 | 3 | | | 9 |
| pA ⃖ HSII-(1.1) | 1.1 | 0.7 | | | |
| pA ⃗ HSII-(1.1) 0 ± | 1.7 0.4 | 0.7 | | | |

TABLE 1-continued

| Plasmids | K562 | HeLa | THP-1 | HL60 | MEL |
| --- | --- | --- | --- | --- | --- |
| pεp | 1 | 1 | | | .03** |
| pεp ≤HSII | N.D. | 1 ± 0.1 | | | 1.16** |
| pεp ≥HSII | 337 | 0.9 | | | 0.24** |
| pεp ≤HSII-(0.8) | 345 | | | | |
| pεp ≥HSII-(0.8)-≥HSI (6.3) | 486* | | | | |
| | 0 | 0.7 | | | |

Table 1.
Relative CAT activities of CAT plasmids driven either by the SV40 or the epsilon-globin promoter.
Relative CAT activity of a test plasmid is defined as the percentage of total input $^{14}$C-chloramphenicol that is converted to the acetylated forms (spots a and b on the TLC), over the percentage of conversion by the enhancerless pA10CAT2 or pεp whose CAT activity is set at 1.
Values in parentheses are relative CAT activities obtained from CAT assays carried out under an improved condition (see FIG. 3 legend).
* = corrected CAT activity of the same number of transfecting pεp ≥HSII (0.8)-≥HSI (6.3) molecules as the other smaller plasmids (see FIG. 5 legend).
**the percentage conversion of $^{14}$C-Chloramphenicol into the acetylated forms is very low as compared to those for the plasmids containing the SV40 promoter. To illustrate this observation, the relative CAT values were therefore calculated using pA10CAT2 as the reference.
N.D. = not done.

For proper regulation of the gene in the cassette in hematopoietic cells, DNA sequences with possible auxiliary regulatory functions underlying major DNase 1 hypersensitive sites HSI, HSIII, HSIV (see FIG. 2) or HSVI (Tuan, D., et al. (1985) Proc. Natl. Acad. Sci. 82 6384) or any combination of these sites may also be spliced next to the erythroid specific enhancer or into other appropriate sites in the cassettes, or in the vector sequence.

Equivalents

Those skilled in the art will recognize, or be able to ascertain using no more than routine experimentation, many equivalents to the specific embodiments of the invention described herein. Such equivalents are intended to be encompassed by the following claims.

We claim:

1. An isolated DNA construct for incorporation into a host cell and for expression of a protein therein, comprising:
   a. DNA comprising a transcription unit comprising a structure gene encoding the protein or a precursor thereof and a promoter to drive transcription of the structural gene; and
   b. a human erythroid-specific transcriptional enhancer element which is identical to an enhancer sequence, having the DNA sequence shown in FIG. 1, wherein its natural location is about 10.3–11.1 kilobases upstream of the human epsilon globin gene and about 53.0–53.8 kilobases upstream of the beta-globin gene in human genomic DNA, the enhancer element being located in sufficient proximity to the transcription unit to enhance transcription thereof.

2. A DNA construct of claim 1, wherein the transcription unit encodes a human globin polypeptide chain.

3. A DNA construct of claim 2, wherein the transcription unit encodes human beta-globin.

4. A DNA construct of claim 1, wherein the structural gene encodes an enzyme or enzyme subunit.

5. A DNA construct of claim 4, wherein the enzyme is glucose-6-phosphate dehydrogenase or pyruvate kinase.

6. A DNA construct of claim 1, wherein the transcription unit encodes an erythroid cell structural protein.

7. A DNA construct of claim 1, wherein the enhancer element consists essentially of a portion of the enhancer element having the sequence shown in FIG. 1 which is transcriptionally functional as an erythroid-specific enhancer.

8. A vector for transferring erythroid cells, precursors thereof or hematopoietic stem cells to produce a transfected cell which expresses a protein of interest, comprising:
   a transcription unit comprising a structural gene encoding the protein of a precursor thereof and a promoter to drive transcription of the gene; and
   b. a human erythroid-specific transcriptional enhancer element, or a portion thereof which is transcriptionally functional as an erythroid-specific enhancer, which is identical to an enhancer sequence, having the DNA sequence shown in FIG. 1, wherein its natural location is about 10.3–11.1 kilobases upstream of the human epsilon globin gene and about 53.0–53.8 kilobases upstream of the beta-globin gene in human genomic DNA, or a portion thereof, which is transcriptionally functional as an erythroid-specific enhancer, the enhancer element being located in sufficient proximity to the transcription unit to enhance transcription thereof.

9. A vector of claim 8, wherein the transcription unit encodes a human globin polypeptide chain.

10. A vector of claim 9, wherein the transcription unit encodes human beta-globin.

11. A vector of claim 8, wherein the structural gene encodes an enzyme or enzyme subunit.

12. A vector of claim 11, wherein the enzyme is glucose-6-phosphate dehydrogenase or pyruvate kinase.

13. A vector of claim 8, wherein the transcription unit encodes an erythroid cell structural protein.

14. A vector of claim 8, further comprising an expressible gene encoding a selectable marker.

15. A vector of claim 8, comprising a plasmid or virus.

16. A vector of claim 8, comprising a retrovirus.

17. A retroviral vector for incorporation into erythroid cells, precursors thereof or hematopoietic stem cells, comprising:
   a. a transcription unit comprising a structural gene encoding a protein which can be synthesized in an erythroid cell and a promoter to drive transcription of the gene;
   b. a human erythroid-specific transcriptional enhancer element consisting essentially of a human, erythroid-specific, transcriptionally functional enhancer element which is identical to an enhancer sequence, having the DNA sequence shown in FIG. 1, wherein its natural location is about 10.3–11.1 kilobases upstream of the human epsilon globin gene and about 53.0–53.8 kilobases upstream of the beta-globin gene in human genomic DNA, or a portion thereof which is transcriptionally functional as an erythroid-specific enhancer, the enhancer element being located in sufficient proximity to the transcription unit to enhance transcription thereof; and
   c. a selectable marker gene and promoter.

18. A retroviral vector of claim 17, wherein the structural gene encodes a normal human globin polypeptide chain.

19. A retroviral vector of claim 18, wherein the structural gene encodes a normal human beta-globin polypeptide.

20. A retrovirus vector of claim 17, wherein structural gene is a normal beta-globin polypeptide chain.

21. A vector for receiving DNA encoding a protein and for transfecting an erythroid cell to produce a transfected erythroid cell which expresses the protein, comprising:
   a. an insertion region for insertion of DNA encoding a protein or a precursor thereof; and
   b. a human erythroid-specific transcriptional enhancer consisting essentially of a human, erythroid-specific, transcriptionally functional enhancer element which is identical to an enhancer sequence, having the DNA sequence shown in FIG. 1, wherein its natural location is about 10.3–11.1 kilobases upstream of the human epsilon globin gene and about 53.0–53.8 kilobases upstream of the beta-globin gene in human genomic DNA, or a portion thereof which is transcriptionally functional as an erythroid-specific enhancer, the enhancer element being located in sufficient proximity to the insertion region to enhance transcription of DNA inserted therein.

22. A vector of claim 21, wherein the insertion region is a DNA sequence encoding a recognition site for a restriction enzyme.

23. A vector of claim 21, further comprising a promoter located upstream of the insertion region.

24. An erythroid cell transfectant for expression of a protein, containing a transfected DNA comprising:
   a. a transcription unit comprising a structural gene encoding the protein or a precursor thereof and a promoter to drive transcription of the gene; and
   b. a human erythroid-specific transcriptional enhancer element consisting essentially of a human, erythroid-specific, transcriptionally functional enhancer element which is identical to an enhancer sequence, having the DNA sequence shown in FIG. 1, wherein its natural location is about 10.3–11.1 kilobases upstream of the human epsilon globin gene and about 53.0–53.8 kilobases upstream of the beta-globin gene in human genomic DNA, or portion thereof which is transcriptionally functional as an erythroid-specific enhancer, the enhancer element being located in sufficient proximity to the transcription unit to enhance transcription thereof.

25. An erythroid cell transfectant of claim 24, wherein the transcription unit encodes a human globin polypeptide chain.

26. An erythroid cell transfectant of claim 25, wherein the transcription unit encodes beta-globin.

* * * * *